United States Patent

Dondio et al.

[11] Patent Number: 5,968,949
[45] Date of Patent: Oct. 19, 1999

[54] SUBSTITUTED HYDROISOQUINOLINE DERIVATIVES AND THEIR USE AS PHARMACEUTICALS

[75] Inventors: Giulio Dondio; Silvano Ronzoni, both of Milan, Italy

[73] Assignee: SmithKline Beecham S.p.A., Milan, Italy

[21] Appl. No.: 09/029,621

[22] PCT Filed: Sep. 12, 1996

[86] PCT No.: PCT/EP96/04036

§ 371 Date: May 29, 1998

§ 102(e) Date: May 29, 1998

[87] PCT Pub. No.: WO97/10216

PCT Pub. Date: Mar. 20, 1997

[30] Foreign Application Priority Data

Sep. 12, 1995 [IT] Italy .................................. MI95A1900

[51] Int. Cl.$^6$ ...................... C07D 217/00; C07D 217/10
[52] U.S. Cl. ........................ 514/307; 546/144; 546/150; 546/151
[58] Field of Search .................... 546/144, 150, 546/151; 514/307

[56] References Cited

U.S. PATENT DOCUMENTS 4,077,954  3/1978  Ripka ........................ 546/149
4,150,135  4/1979  Ripka ........................ 514/307

FOREIGN PATENT DOCUMENTS 2193600  of 1974  France .

OTHER PUBLICATIONS

Judd et al., Journal of Medicinal Chemistry, 35(1), pp. 48–56 (1992).

Primary Examiner—D M Mach
Attorney, Agent, or Firm—Soma G. Simon; William T. King; Charles M. Kinzig

[57] ABSTRACT

According to the present invention, there is provided a compound, or a solvate or salt thereof of formula (I):

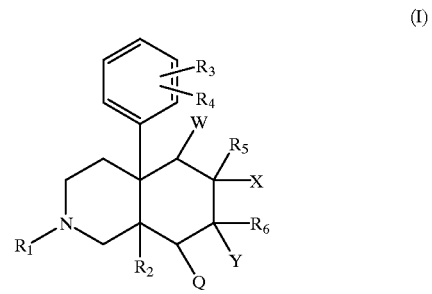

Substituted hydroisoquinoline derivatives are potent and selective delta opioid agonists and antagonists and are of potential therapeutic utility as inter alia analgesics.

10 Claims, No Drawings

SUBSTITUTED HYDROISOQUINOLINE DERIVATIVES AND THEIR USE AS PHARMACEUTICALS

This application is a 371 of PCT/EP96/04036, filed Sep. 12, 1996.

The present invention is concerned with novel substituted hydroisoquinoline derivatives, processes for their preparation and their use in medicine.

The presence of at least three populations of opioid receptors (mu, delta and kappa) is now well established and documented and all three appear to be present in the central and peripheral nervous system of many species including man (Lord J. A. H. et al., Nature 1977, 267, 495).

Activation of all three opioid receptor subtypes can lead to antinociception in animal models. In particular, studies with peptidic delta agonists have indicated that activation of the delta receptor produces antinociception in rodents, primates and can induce clinical analgesia in man (D. E. Moulin et al. Pain, 1985, 23, 213). Evidence exists that suggest a lesser propensity of delta agonists to cause the usual side-effects associated with mu and kappa activation (Galligan et al, J. Pharm. Exp. Ther., 1984, 229, 641).

Hydroisoquinoline derivatives used both as opioid analgesics and as antagonists of pharmacological effects induced by narcotic and psychotomimetic drugs, have already been disclosed (U.S. Pat. No. 273,806, U.S. Pat. No. 4,419,517, Du Pont de Nemours; J. Med. Chem., 1988, 31, 555, Zimmermann, D. M. et al.; J. Med. Chem., 1992, 35, 48, Duncan, B. J. et al.)

A structural characteristic of the compounds disclosed in the documents mentioned above is the presence of a 4a-arylhydroisoquinoline framework optionally substituted with oxygen and/or lower alkyl or lower alkylidene groups. These compounds exert their pharmacological action via a predominant interaction with the mu and kappa opioid receptors.

Hydroisoquinoline derivatives having selectivity for the delta opioid receptor have already been described. All the known derivatives are characterised by an aromatic heterocycle system condensed with the hydroisoquinoline ring. For example, indolo octahydroisoquinoline derivatives are disclosed in EP-A-0,485,636 (Toray Ind.), JP-A-4,368,384 (Toray Ind.), whereas quinolino and quinoxalino octahydroisoquinoline derivatives are disclosed in JP-A-6,275,288 (Toray Ind.). In WO 93/01186 (Dr. Lo Zambeletti), indolo, benzofuro or quinolino octahydroisoquinoline derivatives are disclosed.

We have now discovered a novel class of 4a-arylhydroisoquinoline derivatives substituted with an additional aryl, aralkyl or aralkenyl group which are potent and selective delta opioid agonists and antagonists which may therefore be of potential therapeutic utility as analgesics, immunosuppressants to prevent rejection in organ transplant and skin graft, anti-allergic and anti-inflammatory agents, brain cell protectants, agents for treating drug and alcohol abuse, gastritis, diarrhoea, cardiovascular and respiratory diseases, cough, mental illness, epilepsy and, in general, agents for those pathological conditions which, customarily, can be treated with agonists and antagonists of the delta opioid receptor.

According to the present invention, there is provided a compound, or a solvate or salt thereof of formula (I):

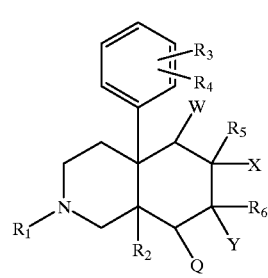

in which, $R_1$ is hydrogen, linear or branched $C_{1-6}$ alkyl, $C_{3-7}$ cycloalkyl, $C_{3-7}$ cycloalkenyl, $C_{4-6}$ cycloalkylalkyl, $C_{3-5}$ alkenyl, aryl, aralkyl or furan-2 or 3-yl alkyl or $(CH_2)_mCOR$ wherein m is 1 to 5 and R represents hydroxy, $OC_{1-5}$ alkyl, $OC_{3-6}$ alkenyl, aryl or aralkyl or $R_1$ is a group A-B wherein A represents $C_{1-10}$ alkylene and B represents substituted or unsubstituted aryl or heteroaryl;

$R_2$ is hydrogen, hydroxy or $C_{1-5}$ alkoxy, preferably methoxy, halogen, nitro, $NR_7R_8$, $SR_7$, where $R_7$ and $R_8$, which may be the same or different, are each hydrogen, linear or branched $C_{1-6}$ alkyl, aryl, aralkyl, or $COR_1$ preferably acetyl;

$R_3$ and $R_4$, which can be the same or different, are each hydrogen, hydroxy, $C_{1-3}$ alkoxy, preferably methoxy, haloalkyl, preferably trifluoromethyl, halogen, SH, $C_{1-4}$-alkylthio, $NHR_7$, $NR_7R_8$, $NHCOR_7$, $NHSO_2R_7$, wherein $R_7$ and $R_8$ have the same meaning described above;

$R_5$ and $R_6$ which may be the same or different are hydrogen or a group

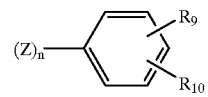

in which n is 0 or 1 and when n=1, Z is $CHR_{14}$, oxygen, sulphur, $NR_{14}$, where $R_{14}$ has the same meaning described below, or ethylene, ethenylene, ethynylene, provided that $R_5$ and $R_6$ are not simultaneously hydrogen;

$R_9$ is hydrogen, hydroxy, $C_{1-5}$ alkoxy, preferably methoxy, halogen, $SR_{11}$, nitro, cyano, $NHR_{11}$ $NR_{11}R_{12}$, $NHCOR_{11}$, $NHSO_2R_{11}$ where $R_{11}$ and $R_{12}$, which may be the same or different, are each hydrogen or $C_{1-6}$ alkyl, preferably methyl, there being up to three $R_9$ in the phenyl ring;

$R_{10}$ is hydrogen, cyano or is a group $C(T)R_{13}$, in which T is oxygen or sulphur, $R_{13}$ is $C_{1-18}$ alkyl, $C_{1-18}$ alkoxy or $NR_{14}R_{15}$, where $R_{14}$ and $R_{15}$, which may be the same or different, are hydrogen, linear or branched $C_{1-6}$ alkyl, $C_{3-7}$ cycloallyl, $C_{4-6}$ cycloalkyalkyl, $C_{3-6}$ alkenyl, aryl, aralkyl or an optionally substituted heterocyclic ring or may form together a $C_{3-6}$ alkyl ring which may be interrupted by an oxygen or a $NR_{14}$ in which $R_{14}$ has the same meaning described above;

X and Y, which may be the same or different, are each hydrogen, hydroxy, $C_{1-5}$ alkoxy, preferably methoxy, $COR_1$ preferably acetyl or together may form a double bond, or;

X or Y may form together with $R_5$ and $R_6$ respectively, an exocyclic double bond, forming a group

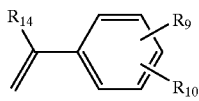

where $R_9$, $R_{10}$ and $R_{14}$ have the same meaning described above, or may form an exocyclic double bond, forming a group

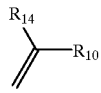

where $R_{10}$ and $R_{14}$ have the same meaning described above with the proviso that $R_{10}$ and $R_{14}$ are not simultaneously hydrogen, or;

X forms together with $R_5$ a C=O group with the proviso that Y and/or $R_6$ may not be hydrogen, hydroxy, lower alkyl or lower alkoxy, or;

Y forms together with $R_6$ a C=O group with the proviso that X and/or $R_5$ may not be hydrogen, hydroxy, lower alkyl or lower alkoxy, and;

Q and W which may be the same or different, are each hydrogen or form a double bond with Y and X respectively.

When $R_1$ is aryl, it is preferably phenyl; when it is aralkyl, it is preferably phenyl-$C_{1-6}$ alkyl.

Examples of $R_1$ are methyl, ethyl.

Examples of $R_2$ are hydrogen.

Examples of $R_3$ and $R_4$ are hydrogen, hydroxy, methoxy in all possible positions of the ring.

Examples of Z are carbon, nitrogen, ethynylene.

Examples of $R_9$ are hydrogen, bromine.

An example of $R_{10}$ is hydrogen.

An example of $R_{14}$ is hydrogen.

Preferably, W and Q are each hydrogen.

A first group of preferred compounds of formula (I) is that in which n=0, $R_6$ is hydrogen and X and Y together form a double bond.

A second group of preferred compounds of formula (I) is that in which n=0, $R_5$ is hydrogen and Y and X together form a double bond.

A third group of preferred compounds of formula (I) is that in which n=1, Z=NH, $R_6$, X and Y are hydrogen.

A fourth group of preferred compounds of formula (I) is that in which n=0, $R_6$ and Y may form together an exocyclic double bond.

Particularly preferred compounds of formula (I) are those in which n=0, $R_6$ is hydrogen, X and Y together form a double bond and $R_9$ and $R_{10}$ are both hydrogen.

More preferred compounds of formula (I) are those in which n=0, $R_5$ and X form together an exocyclic double bond substituted with $R_{10}$, where $R_{10}$ is as defined above.

The compounds of formula (I) or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula (I) or its salt or solvate.

One preferred pharmaceutically acceptable form is the crystalline form, including such form in a pharmaceutical composition. In the case of salts and solvates the additional ionic and solvent moieties must also be non-toxic.

Examples of pharmaceutically acceptable salts of a compound of formula (I) include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

The compounds of formula (I) may exist in more than one stereoisomeric form, and the invention extends to all such forms as well as to their mixtures thereof, including racemates.

In general, the compounds of formula (I) may be prepared by the method illustrated in the following general reaction schemes, or by modification thereof, using readily available starting materials, reagents and conventional synthetic procedures. If a particular enantiomer of a compound of the present invention is desired, it may be synthesised starting from the desired enantiomer of the starting material and performing reactions not involving racemization processes or it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxy, diastereomeric salts are formed with an appropriate optically active acid or base, followed by resolution of diastereomeric salts by fractional crystallization and subsequent recovery of the pure enantiomers.

Compounds of formula (I) in which n=0, $R_6$ and Y are H, X=OH, may be obtained by reacting ketones of formula (II) (J. Org. Chem., 1989, 54, 1442), with lithium derivatives of formula (III), as described in scheme 1:

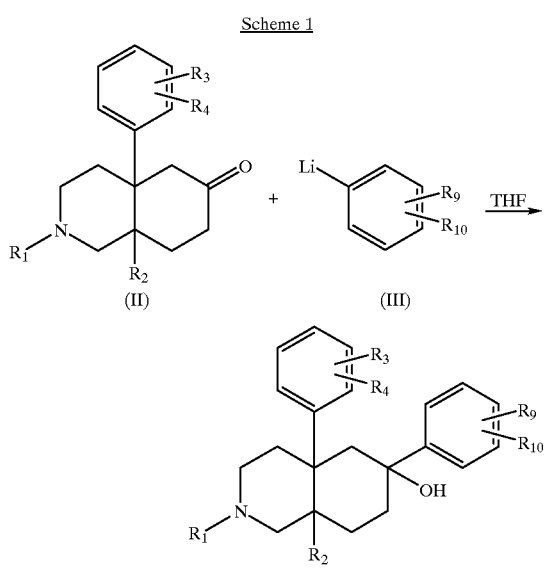

Compounds of formula (I) in which n=0, $R_6$=H, X and Y form together a double bond, may be obtained starting from compounds of formula (I) obtained according to the scheme 1, in the presence of conc. HCl, as described in scheme 2:

Scheme 2

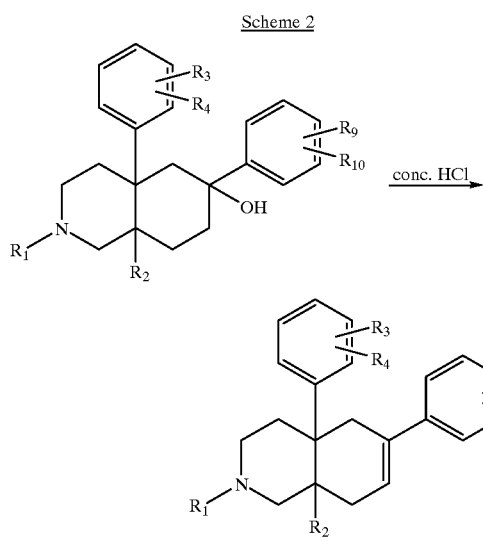

Compounds (I) in which n=1, Z=NH, $R_6$, X and Y are H, may be obtained by reacting ketones of formula (II) with anilines of formula (IV) in the presence of $NaCNBH_3$ in MeOH, as described in scheme 3:

Scheme 3

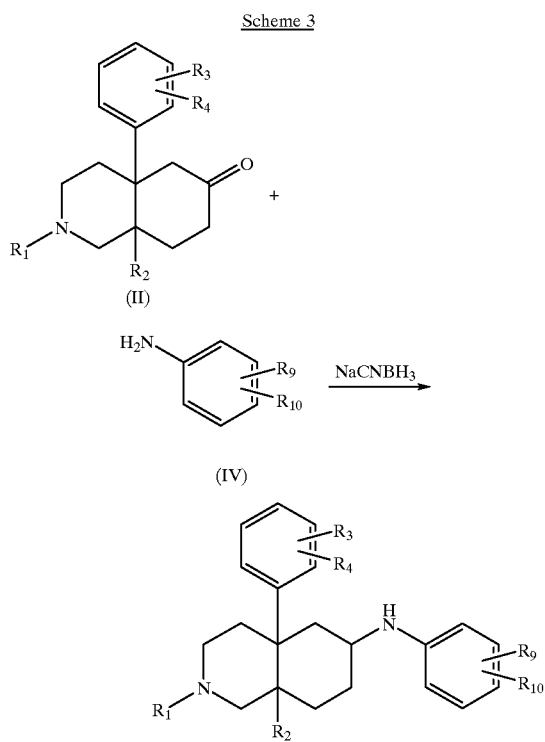

Compounds of formula (I) in which n=1, Z=$CR_{14}$, $R_5$ and X together form a C=O group, may be obtained starting from ketones of formula (II) and aldehydes or ketones of formula (V) by condensation in the presence of a base, as described in scheme 4:

Scheme 4

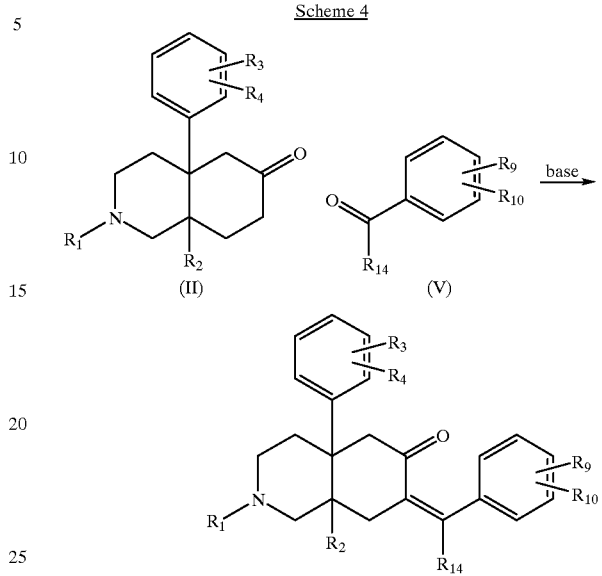

Compounds of formula (I) in which n=1, Z=$CR_{14}$, $R_5$ and X are H, may be obtained starting from ketones of formula (I) obtained according to the scheme 4, treating the corresponding thioketal with Ni Raney in MeOH, as described in scheme 5:

Scheme 5

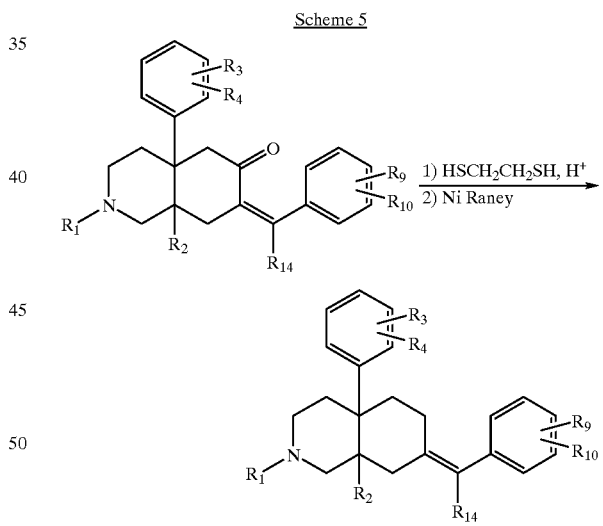

Compounds of formula (I) in which n=1, Z=$CR_{14}$, $R_6$ and Y are H, may be obtained by reacting ketones of formula (II) with phosphonium salts of formula (VI) in the presence of a base in THF; other compounds of general formula (I) may be obtained after acidic treatment of the resulting compound, producing a shift of the double bond inside the ring as described in scheme 6:

Scheme 6

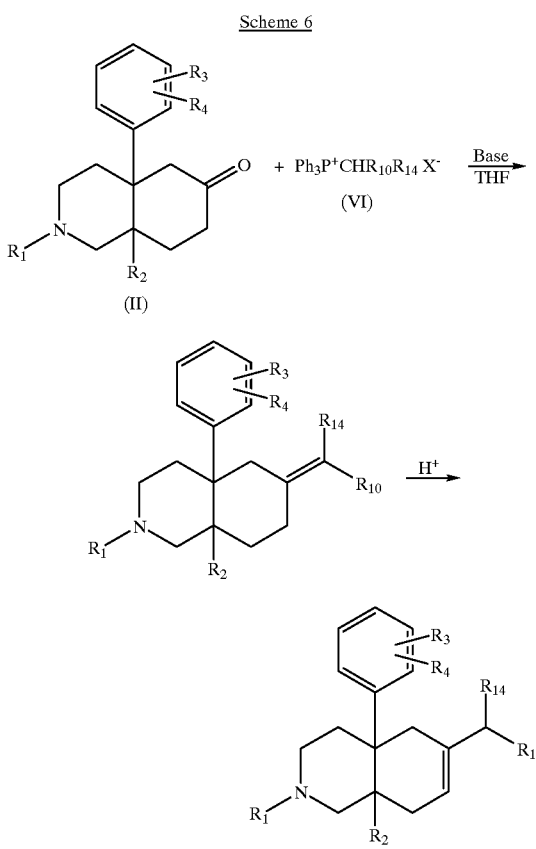

Compounds of formula (I) in which n=1, Z=ethynylene, $R_6$ and Y are H and X=OH may be obtained by reacting ketones of general formula (II) with lithium derivatives of formula (VII) as described in scheme 7

Scheme 7

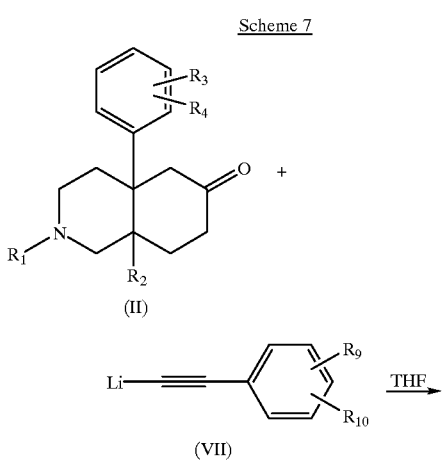

Compounds of formula (I) in which n=1, Z=ethynylene, $R_6$=H, X and Y or W and X form together a double bond, may be obtained starting from compounds of formula (I) obtained according to the scheme 7, in the presence of TsOH in boiling toluene, as described in scheme 8:

Scheme 8

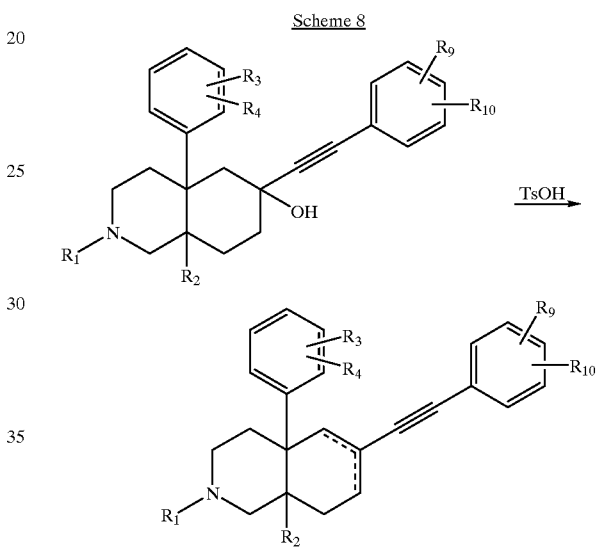

Compounds of formula (I) described herein but substituted in the adjacent position, may be obtained starting from ketones of general formula (VII) (J. Med. Chem., 1992, 35, 48) following the schemes 1–8 described above: The compounds of formula (I) may be converted into their pharmaceutically acceptable salts by reaction with the appropriate organic or mineral acids.

Solvates of the compounds of formula (I) may be formed by crystallization or recrystallization from the appropriate solvent. For example, hydrates may be formed by crystallization or recrystallization from aqueous solutions, or solutions in organic solvents containing water.

Also salts or solvates of the compounds of formula (I) which are not pharmaceutically acceptable may be useful as intermediates in the production of pharmaceutically acceptable salts or solvates. Accordingly such salts or solvates also form part of this invention.

In general compounds of formula (I) acting as selective delta receptor ligands may be useful as analgesics, immunosuppressants to prevent rejection in organ transplant and skin graft, anti-allergic and anti-inflammatory agents, brain cell protectants, for the treatment of drug and alcohol abuse, to decrease gastric secretion, for the treatment of diarrhoea, cardiovascular and respiratory diseases, cough, mental illness, epileptic seizures and other neurologic disorders (herein after referred to as 'Conditions'). In particular, the activity of the compounds of formula (I) as delta agonists in standard tests indicates that they are of potential therapeutic utility as analgesic agents for the amelioration or elimination of pain.

Accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of the Conditions.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known agents for treating the Conditions.

Preferably, a pharmaceutical composition of the invention is in unit dosage form and in a form adapted for use in the medical or veterinarial fields. For example, such preparations may be in a pack form accompanied by written or printed instructions for use as an agent in the treatment of the Conditions.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi- dose forms such as a bottle from which the appropriate dose may be withdrawn or a solid form or concentrate which can be used to prepare an injectable formulation.

The compounds of this invention may also be administered by inhalation, via the nasal or oral routes. Such administration can be carried out with a spray formulation comprising a compound of the invention and a suitable carrier, optionally suspended in, for example, a hydrocarbon propellant.

Preferred spray formulations comprise micronised compound particles in combination with a surfactant, solvent or a dispersing agent to prevent the sedimentation of suspended particles. Preferably, the compound particle size is from about 2 to 10 microns.

A further mode of administration of the compounds of the invention comprises transdermal delivery utilising a skin-patch formulation. A preferred formulation comprises a compound of the invention dispersed in a pressure sensitive adhesive which adheres to the skin, thereby permitting the compound to diffuse from the adhesive through the skin for delivery to the patient For a constant rate of percutaneous absorption, pressure sensitive adhesives known in the art such as natural rubber or silicone can be used.

As mentioned above, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

No unacceptable toxicological effects are expected with the compounds of the invention when administered in accordance with the invention.

The present invention also provides a method for the treatment and/or prophylaxis of the Conditions in mammals, particularly humans, which comprises administering to the mammal in need of such treatment and/or prophylaxis an effective amount of a compound of formula (I) or a pharmaceutically acceptable salt or solvate thereof.

The activity of the compounds of the present invention as selective delta ligands is determined in radioligand binding assays as described below.

Mouse brain membranes were prepared as described by Kosterlitz (*Br. J. Pharmacol.*, 1981, 73, 939.). The binding of the preferential delta ligand [$^3$H]-[D-Ala$^2$,D-Leu$^5$]-enkephalin (DADLE) was evaluated at its $K_D$ concentration (1.3 nM) in presence of 40 nM of the unlabelled mu ligand [D-Ala$^2$, MePhe$^4$, Gly-ol5]-enkephalin (DAMGO). The binding of the mu ligand [$^3$H]-DAMGO (*Eur. J. Pharmacol.*, 1989, 166, 213) and of the kappa ligand [$^3$H]-U69593 (*Excerpta Medica*, 1990, 211) were carried out at 0.5 nM. The non-specific binding was determined in presence of naloxone (10 μM) for all tritiated ligands. Binding data were expressed as percentage of inhibition and fitted the following equation: $f(x)=100.X/(IC_{50}+X)$ where X are cold drug concentration values. The $IC_{50}$ obtained were used to calculate the inhibitory constants ($K_i$) accordingly to the Cheng and Prusoff relation (*Biochem. Pharmacol.*, 1973, 22, 3099).

The delta agonist/antagonist activity of the compounds of the present invention is determined in the mouse vas deferens (MVD) bioassay as described below.

Vasa deferentia were obtained from CD-1 mice and were suspended in a Mg$^{2+}$-free Krebs buffer at 37° C. The tissues were electrically stimulated with pulse trains having the following parameters: train duration 50 ms, stimulus duration 2 ms, frequency of stimuli 50 Hz, maximal voltage 60–70 V, train frequency 0.1 Hz. Concentration response curves for each compounds were constructed cumulatively. Linear regression analysis and $IC_{50}$ concentrations were evaluated according to Tallarida and Murray (*Manual of Pharmacological Calculations*, Springer Verlag N.Y., 1981).

The most potent compounds described in the present invention showed affinities for the delta receptor ranging from 0.5 to 200 nM with delta selectivity ranging from 5 to 1500 times in respect to the other opioid receptor types. The compound of Example 3 was found to be the most potent of the exemplified compounds.

Mouse abdominal constriction (MAC) (*Proc. Soc. Exp. Biol. Med*, 1957, 95, 729), mouse tail-flick (MTF) (*J. Pharm. Exp. Ther.*, 1941, 72, 74) and mouse tail-flick warm water (MTF-WW) (*Life Sci.*, 1986, 39, 1795) were adopted to evaluate the antinociceptive efficacy of the compounds of the present invention.

The following Examples illustrate the preparation of the compounds of the present invention. The compounds of the Examples are summarised in the chemical table.

EXAMPLE 1

(±)-trans-1,2,3,4,4a,5,6,7,8,8a-Decahydro-4a-(3-methoxyphenyl)-2-methyl-6-phenyl-6-isoquinolinol To a solution of 1.1 g (0.04 mol) of (±)-trans-1,2,3,4,4a,5,6,7,8,8a-decahydro4a-(3-methoxyphenyl)-2-methyl-6-isoquinolinone in 50 ml of Et$_2$O and 50 ml of dry THF, under a nitrogen atmosphere and at 0° C., 10.3 ml (0.02 mol) of a 2.0 M solution of phenyllithium in benzene were added dropwise. The reaction mixture was allowed to warm up to room temperature overnight, then it was quenched with a saturated NH$_4$Cl solution. The aqueous phase was extracted with AcOEt, then the combined organic phases were washed with a saturated NaCl solution and dried over Na$_2$SO$_4$. The solvent was removed in vacuo and the residue was purified by flash chromatography, eluting with a mixture CH$_2$Cl$_2$/MeOH/conc. NH$_4$OH 86:10:0.6 respectively, yielding 0.65 g of the title compound.

C$_{23}$H$_{29}$NO$_2$

I.R. (neat): 3580, 2940, 1610, 1580 cm$^{-1}$

EXAMPLE 2

(±)-trans-4a-(3-Methoxyphenyl)-2-methyl-6-phenyl-1,2,3,4,4a,5,8,8a-octahydroisoquinoline A solution of 0.65 g (1.8 mmol) of (±)-trans-1,2,3,4,4a,5,6,7,8,8a-decahydro-4a-(3-methoxyphenyl)-2-methyl-6-phenyl-6-isoquinolinol in 60 ml of 37% HCl was stirred at room temperature for 90 min. The solution was then concentrated in vacuo up to a volume of ca. 10 ml and the pH was adjusted to 14 with 40% NaOH solution. The aqueous phase was extracted with AcOEt, the organic phase was dried over Na$_2$SO$_4$ and the solvent removed in vacuo. The residue was purified by flash chromatography, eluting with a mixture CH$_2$Cl$_2$/MeOH/conc. NH$_4$OH 90:7:0.7 respectively, yielding 0.3 g of the title compound.

C$_{23}$H$_{27}$NO

N.M.R. 300 MHz (CDCl$_3$): δ 7,4–7,0 (m, 8H); 6,7 (m, 1H); 5,95 (m, 1H); 3,8 (s, 3H); 2,9–1,4 (m, 14H).

EXAMPLE 3

(±)-trans-4a-(3-Hydroxyphenyl)-2-methyl-6-phenyl-1,2,3,4,4a,5,8,8a-octahydroisoquinoline 2.7 ml (29 mmol) of boron uibromide were dissolved in 85 ml of dry CHCl$_3$ under a nitrogen atmosphere. 1.6 g (4.8 mmol) of (±)-trans4a-(3-methoxyphenyl)-2-methyl-6-phenyl-1,2,3,4,4a,5,8,8a-octahydroisoquinoline dissolved in 17 ml of dry CHCl$_3$ were added dropwise at room temperature. After 2 h the reaction mixture was poured onto 85 g of crushed ice containing 8.5 ml of conc. NH$_4$OH and stirred 20 min. The phases were separated, the organic phase was dried over Na$_2$SO$_4$ and the solvent removed in vacuo. The residue was purified by flash chromatography, eluting with a mixture CH$_2$Cl$_2$/MeOH/conc. NH$_4$OH 82:13:0.8 respectively. The resulting solid was triturated with acetone, filtered, washed and dried, yielding 0.6 g of the title compound. M.p.=243–246° C.

C$_{22}$H$_{25}$NO

I.R. (KBr): 3420, 2900, 1615, 1575 cm$^{-1}$

N.M.R. 300 MHz (DMSO-d$_6$): δ 9,1 (s, 1H); 7,3–7,1 (m, 5H); 7,0–6,8 (m,3H); 6,5 (m, 1H); 6,0 (m, 1H); 2,9–1,7 (m, 1 1H); 2,2 (s, 3H).

MS (EI) m/z =319,2 (M$^+$).

EXAMPLE 4

(±)-trans-7-Benzylidene-1,2,3,4,4a,5,6,7,8,8a-decahydro4a-(3-methoxyphenyl)-2-methyl-6-isoquinolinone 0.96 g (8.6 mmol) of t-BuOK were suspended in 100 ml of dry THF under a nitrogen atmosphere, and 1.95 g (7.13 mmol) of (±)-trans-1,2,3,4,4a,5,6,7,8,8a-decahydro4a-(3-methoxyphenyl)-2-methyl-6-isoquinolinone dissolved in 50 ml of dry THF were added at −10° C. The temperature was allowed to warm to 10° C. in 1 h, then the reaction mixture was cooled to −10° C. and 0.87 ml (8.6 mmol) of benzaldehyde dissolved in 25 ml of dry THF were added. The reaction mixture was allowed to warm to room temperature and after 2 h it was poured onto $H_2O$ and extracted with AcOEt. The organic phase was dried over $Na_2SO_4$ and the solvent removed in vacuo. The residue was purified by flash chromatography, eluting with a mixture $CH_2Cl_2$/MeOH/conc. $NH_4OH$ 94.5:5:0.5 respectively, yielding 0.85 g of the title compound.

$C_{24}H_{27}NO_2$

I.R. (neat): 2930, 2795, 1680, 1600 cm$^{-1}$

EXAMPLE 5

(±)-trans-7-Benzylidene-1,2,3,4,4a,5,6,7,8,8a-decahydro-4a-(3-hydroxyphenyl)-2-methyl-6-isoquinolinone hydrochloride The reaction was conducted as described in Example 3, using 0.1 g (0.28 mmol) di (±)-trans-7-benzylidene-1,2,3,4,4a,5,6,7,8,8a-decahydro-2-methyl-4a-(3-methoxyphenyl)-6-isoquinolinone, 0.16 ml (1.7 mmol) of boron tribromide and 6 ml of dry $CHCl_3$. The crude reaction mixture was purified by flash chromatography, eluting with a mixture $CH_2Cl_2$/MeOH/conc. $NH_4OH$ 86:10:0.6 respectively. The resulting solid was dissolved in MeOH and the solution brought to acidic pH with $Et_2O$/HCl. The solvent was removed in vacuo, the resulting solid was triturated with acetone, yielding 0.07 g of the title compound. M.p.= 256–260° C.

$C_{23}H_{25}NO_2 \cdot HCl$

I.R. (KBr): 3100, 2880, 2580, 1680, 1595 cm$^{-1}$

N.M.R. 300 MHz ($CD_3OD$): δ 7,5–6,5 (m, 10H); 3,7–1,8 (m, 11H); 2,4 (s, 3H).

EXAMPLE 6

(±)-trans-1,2,3,4,4a,5,6,7,8,8a-Decahydro-2-methyl-4a-(3-methoxyphenyl)-6-phenylamino isoquinoline To a solution of 4 g (12.9 mmol) of (±)-trans-1,2,3,4,4a,5,6,7,8,8a-decahydro-4a-(3-methoxyphenyl)-2-methyl-6-isoquinolinone in 60 ml of MeOH, under a nitrogen atmosphere and at room temperature, 1 ml of MeOH/HCl was added. The solution was cooled to 10° C. and 6.6 ml (77.5 mmol) of aniline were added. The reaction mixture was allowed to warm to room temperature and after 15 min 16 g of 4 Å molecular sieves were added. After 1 h 0.48 g (7.7 mmol) of $NaCNBH_3$ were added portionwise and the resulting mixture stirred overnight. The reaction mixture was then filtered over a fritted glass funnel and the solvent removed in vacuo. The residue was taken up in water, brought to pH 14 with a 20% NaOH solution and extracted with AcOEt. The combined organic extracts were dried over $Na_2SO_4$ and the solvent removed in vacuo. The crude reaction mixture was purified by flash chromatography, eluting with a mixture $CH_2Cl_2$/MeOH/conc. $NH_4OH$ 92:8:0.5 respectively, yielding 0.86 g of the title compound.

$C_{23}H_{30}N_2O$

I.R. (neat): 3420, 2920, 1600, 1505 cm$^{-1}$

N.M.R. 300 MHz ($CDCl_3$): δ 7,3–6,5 (m, 9H); 6 (s, 3H); 3,1–1,9 (m, 14H); 1,2 (s, 3H).

EXAMPLE 7

(±)-trans-1,2,3,4,4a,5,6,7,8,8a-Decahydro-4a-(3-hydroxyphenyl)-2methyl-6-phenylamino isoquinoline The reaction was conducted as described in Example 3, using 0.25 g (0.71 mmol) of (±)-trans-1,2,3,4,4a,5,6,7,8,8a-decahydro-4a-(3-methoxyphenyl)-2-methyl-6-phenylaminoisoquinoline, 0.4 ml (4.3 mmol) of boron tribromide and 14 ml of dry $CHCl_3$. The crude reaction mixture was purified by flash chromatography, eluting with a mixture $CH_2Cl_2$/MeOH/conc. $NH_4OH$ 86:10:0.6 respectively, yielding 0.18 g of the title compound. M.p.= 235–237° C.

$C_{22}H_{28}N_2O$

I.R. (KBr): 3410, 2920, 1600, 1510 cm$^{-1}$

N.M.R. 80 MHz ($CDCl_3$): δ 9,1 (bs, 1H); 7,3–5,8 (m, 9H); 3,1–1,9 (m, 15H); 2,2 (s, 3H).

EXAMPLE 8

(±)-trans-6-(3-Bromophenyl)-1,2,3,4,4a,5,6,7,8,8a-decahydro-2-ethyl-4a-(3-methoxyphenyl)-6-isoquinolinol 8.9 ml (12.5 mmol) of a 1.4 M solution of n-butyllithium in hexane were added dropwise, under a nitrogen atmosphere and at −55° C., to a solution of 2.95 g (12.5 mmol) of 1,3-dibromobenzene in 10 ml of dry THF. After 90 min this solution was added via cannula to a solution of 1.2 g (4.17 mmol) of (±)-trans-1,2,3,4,4a,5,6,7,8,8a-decahydro-2-ethyl-4a-(3-methoxyphenyl)-6-isoquinolinone in 10 ml of dry THF and at −20° C. The reaction mixture was allowed to warm up to room temperature overnight, then it was quenched with a saturated $NH_4Cl$ solution. The aqueous phase was extracted with AcOEt and the solvent was removed in vacuo. The residue was taken up in $Et_2O$ and washed with a 10% HCl solution; the phases were separated and the aqueous phase was brought to pH 14 with a 2N NaOH solution, then extracted with $CH_2Cl_2$. The organic phase was dried over $Na_2SO_4$, the solvent was removed in vacuo and the crude reaction mixture was purified by flash chromatography, eluting with a mixture $CH_2Cl_2$/MeOH/conc. $NH_4OH$ 94.5:5:0.5 respectively, yielding 0.44 g of the title compound.

$C_{24}H_{30}BrNO_2$

I.R. (neat): 3580, 2930, 1610, 1580 cm$^{-1}$.

EXAMPLE 9

(±)-trans-6-(3-Bromophenyl)-2-ethyl4a-(3-methoxyphenyl)-1,2,3,4,4a,5,8,8a-octahydroisoquinoline The reaction was conducted as described in Example 2, using 0.44 g (0.99 mmol) of (±)-trans-6-(3-bromophenyl)-1,2,3,4,4a,5,6,7,8,8a-decahydro-2-ethyl-4a-(3-methoxyphenyl)-6-isoquinolinol and 15 ml of 37% HCl. The crude reaction mixture was purified by flash chromatography, eluting with a mixture $CH_2Cl_2$/MeOH/conc. $NH_4OH$ 98:2:0.4 respectively, yielding 0.25 g of the title compound.

$C_{24}H_{28}BrNO$

I.R. (neat): 2940, 2820, 1605, 1580 cm$^{-1}$.

N.M.R. 300 MHz (DMSO-$d_6$): δ 7.5–7.1 (m, 7H); 6.7 (d, 1H); 6.1 (s, 1H); 3.7 (s, 3H); 2.9–2.1 (m, 11H); 1.8–1.7 (m, 2H); 1.0 (t, 3H).

MS (EI) m/z: 425, 427(M$^+$).

EXAMPLE 10

(±)-trans-6-(3-Bromophenyl)-2,ethyl-4a-(3hydroxyphenyl)-1,2,3,4,4a,5,8,8a-octahydroisoquinoline 0.145 ml (1.14 mmol) of chlorotrimethylsilane were added dropwise to a solution of 0.24 g (0.57 mmol) of (±)-trans-6-(3-bromophenyl)-2-ethyl-4a-(3-methoxyphenyl)-1,2,3,4,4a,5,8,8a-octahydroisoquinoline and 0.17 g (1.14 mmol) of NaI in 5 ml of acetonitrile, under a nitrogen atmosphere and at room temperature. The reaction mixture was refluxed overnight, then it was cooled to room temperature and water was added. The aqueous phase was extracted with AcOEt, the organic phase was washed with a 10% $Na_2S_2O_3$ solution, then dried over $Na_2SO_4$ and the solvent was removed in vacuo. The crude reaction mixture was purified by flash chromatography, eluting with a mixture $CH_2Cl_2$/MeOH/conc. $NH_4OH$ 90:7:0.7 respectively. The resulting solid was triturated with acetone, yielding 0.09 g of the title compound. M.p.=233–225° C.

$C_{23}H_{26}BrNO$

I.R. (KBr): 3400, 2920, 1580, 1475 cm$^{-1}$.

N.M.R. 300 MHz (DMSO-d$_6$): δ 8.9 (s, 1H); 7.4–7.1 (m, 4H); 7.0–6.8 (m, 3H); 6.5 (d, 1H); 6.1 (s, 1H); 2.8–2.1 (m, 11H); 1.8–1.7 (m, 2H); 1.0 (t, 3H).

MS (EI) m/z: 411, 413 (M$^+$).

EXAMPLE 11

(±)-trans-1,2,3,4,4a,5,6,7,8,8a-Decahydro-2-ethyl-4a-(3-methoxyphenyl)-6-phenyl-6-isoquinolinol 30 ml (41.7 mmol) of a 1.4 M solution of n-butyllithium in hexane were added dropwise, under a nitrogen atmosphere and at –55° C., to a solution of 6.5 g (41.7 mmol) of bromobenzene in 30 ml of dry THF. After 1 h the solution was allowed to warm up to –20° C. and a solution of 2.4 g (8.3 mmol) of (±)-trans-1,2,3,4,4a,5,6,7,8,8a-decahydro-2-ethyl-4a-(3-methoxyphenyl)-6-isoquinolinone in 20 ml of dry THF was added. The reaction mixture was allowed to warm up to room temperature overnight, then it was quenched with 30 ml of a 5% HCl solution and the phases were separated. The aqueous phase was extracted with AcOEt, then brought to pH 14 with a 2N NaOH solution and extracted with AcOEt. The organic phase was dried over $Na_2SO_4$ and the solvent was removed in vacuo. The crude reaction mixture was purified by flash chromatography, eluting with a mixture $CH_2Cl_2$/MeOH/conc. $NH_4OH$ 90:7:0.7 respectively, yielding 0.79 g of the title compound.

$C_{24}H_{31}NO_2$

I.R. (KBr): 3580, 2940, 1605, 1580 cm$^{-1}$.

EXAMPLE 12

(±)-trans-2-Ethyl-4a-(3-methoxyphenyl)-6-phenyl-1,2,3,4,4a,5,8,8a-octahydroisoquinoline The reaction was conducted as described in Example 2, using 0.79 g (2.16 mmol) of (±)-trans-1,2,3,4,4a,5,6,7,8,8a-decahydro-2-ethyl-4a-(3-methoxyphenyl)-6-phenyl-6-isoquinolinol and 30 ml of 37% HCl, yielding 0.77 g of the title compound. $C_{24}H_{29}NO$ I.R. (neat): 2940, 1610, 1580, 1240 cm$^{-1}$.

EXAMPLE 13

(±)-trans-2-Ethyl-4a-(3-hydroxyphenyl)-6-phenyl-1,2,3,4,4a,5,8,8a-octahydroisoquinoline The reaction was conducted as described in Example 10, using 0.77 g (2.2 mmol) of (±)-trans-2-ethyl-4a-(3-methoxyphenyl)-6-phenyl-1,2,3,4,4a,5,8,8a-octahydroisoquinoline, 1.32 g (8.8 mmol) of NaI, 1.1 ml (8.8 mmol) of chlorotrimethylsilane and 20 ml of acetonitrile. The crude reaction mixture was purified by flash chromatography, eluting with a mixture $CH_2Cl_2$/MeOH/conc. $NH_4OH$ 90:7:0.7 respectively. The resulting solid was triturated in acetone, yielding 0.115 g of the title compound. M.p.=215–218° C. $C_{23}H_{27}NO$ I.R. (KBr): 3400, 2905, 1580, 1495 cm$^{-1}$.

N.M.R. 300 MHz (DMSO-d$_6$): δ 9.0 (s, 1H); 7.3–6.8 (m, 8H); 6.5 (d, 1H); 6.0 (s, 1H); 2.8–2.1 (m, 1H); 1.8–1.7 (m, 2H); 1.0 (t, 3H).

MS (EI) m/z: 333.1 (M$^+$).

EXAMPLE 14

(±)-trans-6-Benzylidene-1,2,3,4,4a,5,6,7,8,8a-decahydro-2-ethyl-4a-(3-methoxyphenyl)isoquinoline 9.9 ml (13.9 mmol) of a 1.4 M solution of n-butyllithium in hexane were added dropwise, under a nitrogen atmosphere and at room temperature, to a suspension of 5.4 g (13.9 mmol) of benzyltriphenylphosphonium chloride in 30 ml of dry THF. The reaction mixture was stirred for 1 h, then a solution of 1 g (3.5 mmol) of (±)-trans-1,2,3,4,4a,5,6,7,8,8a-decahydro-2-ethyl-4a-(3-methoxyphenyl)-6-isoquinolinone in 10 ml of dry THF was added. The reaction mixture was refluxed 4 h, then cooled and poured onto water and the aqueous phase was extracted with AcOEt. The organic phase was dried over $Na_2SO_4$ and the solvent removed in vacuo. The crude reaction mixture was purified by flash chromatography, eluting with a mixture $CH_2Cl_2$/MeOH/conc. $NH_4OH$ 90:7:0.7 respectively, yielding 0.94 g of the title compound.

$C_{25}H_{31}NO$

I.R. (neat): 2940, 1600, 1580, 1240 cm$^{-1}$.

MS (EI) m/z: 361.2 (M$^+$).

EXAMPLE 15

(±)-trans-6-Benzyl-2-ethyl-4a-(3-hydroxyphenyl)-1,2,3,4,4a,5,8,8a-octahydroisoquinoline The reaction was conducted as described in Example 10, using 0.93 g (2.6 mmol) of (±)-trans-6-benzylidene-1,2,3,4,4a,5,6,7,8,8a-decahydro-2-ethyl4a-(3-methoxyphenyl)isoquinoline, 1.54 g (10.3 mmol) of NaI, 1.3 ml (10.3 mmol) of chlorotrimethylsilane and 20 ml of acetonitrile. The crude reaction mixture was purified by flash chromatography, eluting with a mixture $CH_2Cl_2$/MeOH/conc. $NH_4OH$ 90:7:0.7 respectively. The resulting solid was crystallised from $Et_2O$, yielding 0.09 g of the title compound. M.p.=160–162° C.

$C_{24}H_{29}NO$

I.R. (KBr): 3400, 2910, 1580, 1495 cm$^{-1}$.

N.M.R. 300 MHz (CDCl$_3$): δ 7.2–7.0 (m, 4H); 6.9–6.8 (m,3H); 6.6 (m, 2H); 65.5 (s, 1H); 3.1 (m, 2H); 2.9–2.7 (m, 2H); 2.6–2.1 (m, 7H); 2.1–1.8 (m, 3H); 1.7 (m,1H); 1.0 (t, 3H).

MS (EI) m/z: 347.2 (M$^+$).

EXAMPLE 16

(±)-trans-2-Ethyl-1,2,3,4,4a,5,6,7,8,8a-decahydro-4a-(3-methoxyphenyl)-6-phehylethynyl-6-isoquinolinol To a solution of 3.55 g (34.8 mmol) of phenylacetylene in 30 ml of dry THF, under a nitrogen atmosphere and at –20° C., 24.85 ml (34.8 mmol) of a 1.4 M solution of n-butyllithium in hexane were added. After 1 h a solution of 2 g (7 mmol) of (±)-trans-1,2,3,4,4a,5,6,7,8,8a-decahydro-2-ethyl-4a-(3-methoxyphenyl)-6-isoquinolinone in 20 ml of dry THF was added. The reaction mixture was allowed to warm up to room temperature overnight, then it was quenched with 30 ml of a 5% HCl solution and the phases were separated. The aqueous phase was extracted with $Et_2O$ then brought to pH 14 with a 2N NaOH solution and extracted with AcOEt. The organic phase was dried over $Na_2SO_4$ and the solvent removed in vacuo, yielding 2.38 g of the title compound.

$C_{26}H_{31}NO_2$

I.R. (KBr): 3420, 2940, 1610, 1580 $cm^{-1}$.

EXAMPLE 17

(±)-trans-2-Ethyl-4a-(3-methoxyphenyl)-1,2,3,4,4a,7,8,8a-octahydro-6-phenylethynylisoquinoline hydrochloride A solution of 2.38 g (6.1 mmol) of (±)-trans-1,2,3,4,4a,5,6,7,8,8a-decahydro-2-ethyl-4a-(3-methoxyphenyl)-6-phenylethynyl-6-isoquinolinol and 1.4 g (7.3 mmol) of p-toluenesulfonic acid in 70 ml of toluene was refluxed for 24 h. The solvent was removed in vacuo, and the residue was taken up with $H_2O$, brought to pH 14 with a 2N NaOH solution and the aqueous phase was extracted with $CH_2Cl_2$. The organic phase was dried over $Na_2SO_4$ and the solvent was removed in vacuo. The crude reaction mixture was purified by flash chromatography, eluting with a mixture $(i-Pr)_2O/MeOH/conc.$ $NH_4OH$ 90:10:0.5 respectively, yielding 0.25 g of the compound with greater Rf which were dissolved in acetone. The solution was brought to acidic pH with $Et_2O$/HCl and the solvent removed in vacuo. The resulting solid was triturated with $Et_2O$, yielding 0.2 g of the title compound. M.p.=208–210° C.

$C_{26}H_{29}NO.HCl$

I.R. (KBr): 3440, 2960, 2460, 1580 $cm^{-1}$.

N.M.R. 300 MHz (base libera, $CDCl_3$): δ 7.4 (m, 2H); 7.3–7.2 (m,4H); 7.0 (m, 2H); 6.7 (d, 1H); 6.2 (s, 1H); 3.8 (s, 3H); 2.9–1.6 (m, 13H); 1.0 (t, 3H).

MS (El) m/z: 371.2 ($M^+$).

EXAMPLE 18

(±)-trans-2Ethyl-4a-(3-methoxyphenyl)-1,2,3,4,4a,5,8,8a-octahydro-6-phenylethynylisoquinoline hydrochloride Continuing the elution described in Example 17, 0.89 g of a product with lower Rf were obtained and dissolved in acetone. The solution was brought to acidic pH with $Et_2O$/HCl and the solvent removed in vacuo. The resulting solid was triturated with $Et_2O$, yielding 0.9 g of the title compound. M.p.=183–185° C.

$C_{26}H_{29}NO.HCl$

I.R. (KBr): 3440, 2960, 2460, 1580 $cm^{-1}$.

N.M.R. 300 MHz (base libera, $CDCl_3$): δ 7.4–7.2 (m, 6H); 7.0 (m, 2H); 6.7 (d, 1H); 6.1 (s, 1H); 3.8 (s, 3H); 2.9–1.6 (m, 13H); 1.0 (t, 3H).

MS (EI) m/z: 371.2 ($M^+$).

Chemical table

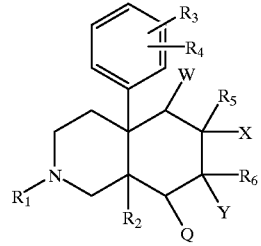

(I)

| Ex. n. | $R_1$ | $R_2$ | $R_3$ | $R_4$ | $R_5$ | W | X | Y | $R_6$ | Q | molecular formula | M.p. ° C. |
|---|---|---|---|---|---|---|---|---|---|---|---|---|
| 1 | Me | H | H | MeO | Ph | H | OH | H | H | H | $C_{23}H_{29}NO_2$ | oil |
| 2 | Me | H | H | MeO | Ph | H | C=C | | H | H | $C_{23}H_{27}NO$ | oil |
| 3 | Me | H | H | OH | Ph | H | C=C | | H | H | $C_{22}H_{25}NO$ | 243–246 |
| 4 | Me | H | H | OMe | C=O | H | —Ph | | H | | $C_{24}H_{27}NO_2$ | oil |
| 5 | Me | H | H | OH | C=O | H | —Ph | | H | | $C_{23}H_{25}NO_2.HCl$ | 256–260 |
| 6 | Me | H | H | OMe | NHPh | H | H | H | H | H | $C_{23}H_{30}N_2O$ | — |
| 7 | Me | H | H | OH | NHPh | H | H | H | H | H | $C_{22}H_{28}N_2O$ | 235–237 |
| 8 | Et | H | H | OMe | 3-BrPh | H | OH | H | H | H | $C_{24}H_{30}BrNO_2$ | oil |
| 9 | Et | H | H | OMe | 3-BrPh | H | C=C | | H | H | $C_{24}H_{28}BrNO$ | oil |
| 10 | Et | H | H | OH | 3-BrPh | H | C=C | | H | H | $C_{23}H_{26}BrNO$ | 223–225 |
| 11 | Et | H | H | OMe | Ph | H | OH | H | H | H | $C_{24}H_{31}NO_2$ | — |
| 12 | Et | H | H | OMe | Ph | H | C=C | | H | H | $C_{24}H_{29}NO_2$ | oil |

-continued

Chemical table

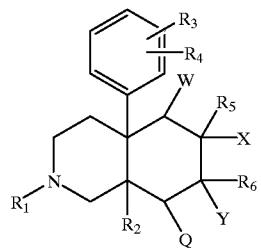

(I)

| Ex. n. | $R_1$ | $R_2$ | $R_3$ | $R_4$ | $R_5$ | W | X | Y | $R_6$ | Q | molecular formula | M.p. °C. |
|---|---|---|---|---|---|---|---|---|---|---|---|---|
| 13 | Et | H | H | OH | Ph | H | C=C | | H | H | $C_{23}H_{27}NO$ | 215–218 |
| 14 | Et | H | H | OMe | ⟨CH=CH–Ph⟩ | H | | H | H | H | $C_{25}H_{31}NO$ | oil |
| 15 | Et | H | H | OH | $CH_2Ph$ | H | C=C | | H | H | $C_{24}H_{29}NO$ | 160–162 |
| 16 | Et | H | H | OMe | C≡CPh | H | OH | H | H | H | $C_{26}H_{31}NO_2$ | — |
| 17 | Et | H | H | OMe | C≡CPh | C=C | | H | H | H | $C_{26}H_{29}NO.HCl$ | 208–210 |
| 18 | Et | H | H | OMe | C≡CPh | H | C=C | | H | H | $C_{26}H_{29}NO.HCl$ | 183–185 |

We claim:

1. A compound, or a solvate or salt thereof, of formula (I):

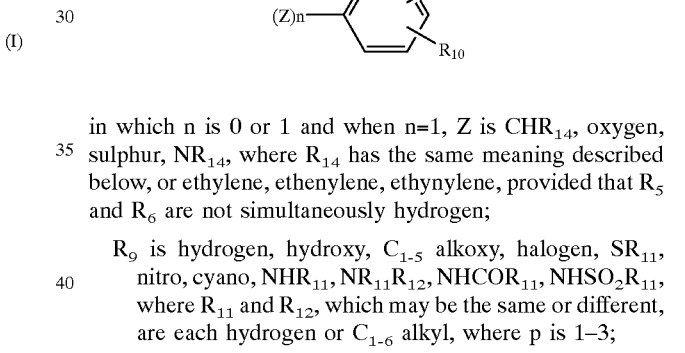

in which, $R_1$ is hydrogen, linear or branched $C_{1-6}$ alkyl, $C_{3-7}$ cycloalkyl, $C_{3-7}$ cycloalkenyl, $C_{4-6}$ cycloalkylalkyl, $C_{3-5}$ alkenyl, aryl, aralkyl or furan-2 or 3-yl alkyl or $(CH_2)_m COR$ wherein m is 1 to 5 and R represents hydroxy, $OC_{1-5}$ alkyl, $OC_{3-6}$ alkenyl, aryl or aralkyl or $R_1$ is a group A-B wherein A represents $C_{1-10}$ alkylene and B represents substituted or unsubstituted aryl or heteroaryl;

$R_2$ is hydrogen, hydroxy or $C_{1-5}$ alkoxy, halogen, nitro, $NR_7R_8$, $SR_7$, where $R_7$ and $R_8$, which may be the same or different, are each hydrogen, linear or branched $C_{1-6}$ alkyl, aryl, aralkyl, or $COR_1$;

$R_3$ and $R_4$, which can be the same or different, are each hydrogen, hydroxy, $C_{1-3}$ alkoxy, haloalkyl, halogen, SH, $C_{1-4}$-alkylthio, $NHR_7$, $NR_7R_8$, $NHCOR_7$, $NHSO_2R_7$, wherein $R_7$ and $R_8$ have the same meaning described above;

$R_5$ and $R_6$ which may be the same or different are hydrogen or a group $$\text{(Z)}_n\!-\!\!\begin{array}{c}\diagup\!\!\!\diagdown\!\!R_9(P)\\ \diagdown\!\!\!\diagup\!\!R_{10}\end{array}$$

in which n is 0 or 1 and when n=1, Z is $CHR_{14}$, oxygen, sulphur, $NR_{14}$, where $R_{14}$ has the same meaning described below, or ethylene, ethenylene, ethynylene, provided that $R_5$ and $R_6$ are not simultaneously hydrogen;

$R_9$ is hydrogen, hydroxy, $C_{1-5}$ alkoxy, halogen, $SR_{11}$, nitro, cyano, $NHR_{11}$, $NR_{11}R_{12}$, $NHCOR_{11}$, $NHSO_2R_{11}$, where $R_{11}$ and $R_{12}$, which may be the same or different, are each hydrogen or $C_{1-6}$ alkyl, where p is 1–3;

$R_{10}$ is hydrogen, cyano or is a group $C(T)R_{13}$, in which T is oxygen or sulphur, $R_{13}$ is $C_{1-18}$ alkyl, $C_{1-18}$ alkoxy or $NR_{14}R_{15}$, where $R_{14}$ and $R_{15}$, which may be the same or different, are hydrogen, linear or branched $C_{1-6}$ alkyl, $C_{3-7}$ cycloalkyl, $C_{4-6}$ cycloalkylalkyl, $C_{3-6}$ alkenyl, aryl, aralkyl or an optionally substituted heterocyclic ring or may form together a $C_{3-6}$ alkyl ring which may be interrupted by an oxygen or a $NR_{14}$ in which $R_{14}$ has the same meaning described above;

X and Y, which may be the same or different, are each hydrogen, hydroxy, $C_{1-5}$ alkoxy, $COR_1$ or together may form a double bond, or;

X or Y may form together with $R_5$ and $R_6$ respectively, an exocyclic double bond, forming a group

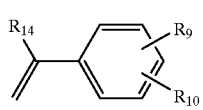

where $R_9$, $R_{10}$ and $R_{14}$ have the same meaning described above, or may form an exocyclic double bond, forming a group

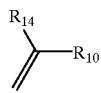

where $R_{10}$ and $R_{14}$ have the same meaning described above, with the proviso that when $R_{10}$ is hydrogen, $R_{14}$ is not hydrogen or methyl, or;

X forms together with $R_5$ a C=O group with the proviso that Y and/or $R_6$ may not be hydrogen, hydroxy, lower alkyl or lower alkoxy, or;

Y forms together with $R_6$ a C=O group with the proviso that X and/or $R_5$ may not be hydrogen, hydroxy, lower alkyl or lower alkoxy, and;

Q and W which may be the same or different, are each hydrogen or form a double bond with Y and X respectively.

2. A compound according to claim 1 in which $R_1$ is methyl, ethyl, phenyl or phenyl-$C_{1-6}$ alkyl.

3. A compound according to claim 1 in which $R_2$ is hydrogen, and $R_3$ and $R_4$ are each independently hydrogen, hydroxy or methoxy.

4. A compound according to claim 1 in which $R_9$ is hydrogen or bromine, and $R_{10}$ is hydrogen.

5. A compound according to claim 1 in which W and Q are each hydrogen.

6. A compound selected from:

(±)-trans-1,2,3,4,4a,5,6,7,8,8a-Decahydro-4a-(3-methoxyphenyl)-2-methyl-6-phenyl-6-isoquinolinol;

(±)-trans-4a-(3-Methoxyphenyl)-2-methyl-6-phenyl-1,2,3,4,4a,5,8,8a-octahydroisoquinoline;

(±)-trans-4a-(3-Hydroxyphenyl)-2-methyl-6-phenyl-1,2,3,4,4a,5,8,8a-octahydroisoquinoline;

(±)-trans-7-Benzylidene-1,2,3,4,4a,5,6,7,8,8a-decahydro-4a-(3-methoxyphenyl)-2-methyl-6-isoquinolinone;

(±)-trans-7-Benzylidene-1,2,3,4,4a,5,6,7,8,8a-decahydro-4a-(3-hydroxyphenyl)-2-methyl-6-isoquinolinone hydrochloride;

(±)-trans-1,2,3,4,4a,5,6,7,8,8a-Decahydro-2-methyl-4a-(3-methoxyphenyl)-6-phenylamino isoquinoline;

(±)-trans-1,2,3,4,4a,5,6,7,8,8a-Decahydro-4a-(3-hydroxyphenyl)-2-methyl-6-phenylamino isoquinoline;

(±)-trans-6-(3-Bromophenyl)-1,2,3,4,4a,5,6,7,8,8a-decahydro-2-ethyl-4a-(3-methoxyphenyl)-6-isoquinolinol;

(±)-trans-6-(3-Bromophenyl)-2-ethyl-4a-(3-methoxyphenyl)-1,2,3,4,4a,5,8,8a-octahydroisoquinoline;

(±)-trans-6-(3-Bromophenyl)-2-ethyl-4a-(3-hydroxyphenyl)-1,2,3,4,4a,5,8,8a-octahydroisoquinoline;

(±)-trans-1,2,3,4,4a,5,6,7,8,8a-Decahydro-2-ethyl-4a-(3-methoxyphenyl)-6-phenyl-6-isoquinolinol:

(±)-trans-2-Ethyl-4a-(3-methoxyphenyl)-6-phenyl-1,2,3,4,4a,5,8,8a-octahydroisoquinoline;

(±)-trans-2-Ethyl-4a-(3-hydroxyphenyl)-6-phenyl-1,2,3,4,4a,5,8,8a-octahydroisoquinoline;

(±)-trans-6-Benzylidene-1,2,3,4,4a,5,6,7,8,8a-decahydro-2-ethyl-4a-(3-methoxyphenyl)isoquinoline;

(±)-trans-6-Benzyl-2-ethyl-4a-(3-hydroxyphenyl)-1,2,3,4,4a,5,8,8a-octahydroisoquinoline;

(±)-trans-2-Ethyl-1,2,3,4,4a,5,6,7,8,8a-decahydro-4a-(3-methoxyphenyl)-6-phehylethynyl-6-isoquinolinol;

(±)-trans-2-Ethyl-4a-(3-methoxyphenyl)-1,2,3,4,4a,7,8,8a-octahydro-6-phenylethynylisoquinoline hydrochloride, and;

(±)-trans-2-Ethyl-4a-(3-methoxyphenyl)-1,2,3,4,4a,5,8,8a-octahydro-6-phenylethynylisoquinoline hydrochloride.

7. A method for treating a pathological condition mediated by a delta opioid receptor, which comprises administering a compound according to claim 1.

8. A method according to claim 7 for the treatment or prophylaxis of pain, allergy or inflammation, brain cell degeneration, drug or alcohol abuse, gastritis, diarrhoea, cardiovascular or respiratory diseases, cough, mental illness, or neurological disorders, which comprises administering a compound according to claim 1.

9. A method for treating organ transplant or skin graft rejection which comprises administering a compound according to claim 1.

10. A pharmaceutical composition comprising a compound according to claim 1 and a pharmaceutically acceptable carrier.

* * * * *